United States Patent [19]

Hori et al.

[11] Patent Number: 4,813,963
[45] Date of Patent: Mar. 21, 1989

[54] FEMORAL COMPONENT FOR A HIP PROSTHESIS

[75] Inventors: Roy Y. Hori; Mark A. Lazzeri, both of Warsaw; Clayton R. Miller, Bremen; Dale A. DeGroff, Goshen; Ted L. Dock, Warsaw, all of Ind.

[73] Assignee: Zimmer, Inc., Warsaw, Ind.

[21] Appl. No.: 88,362

[22] Filed: Aug. 24, 1987

[51] Int. Cl.$^4$ .............................................. A61F 2/32
[52] U.S. Cl. .................................................... 623/23
[58] Field of Search ........................ 623/16, 18, 22, 23

[56] References Cited

U.S. PATENT DOCUMENTS

| D. 283,731 | 2/1986 | Kenud | D 24/33 |
|---|---|---|---|
| 3,605,123 | 3/1971 | Hahn | 3/1 |
| 3,906,550 | 9/1975 | Rostoker et al. | 3/1.912 |
| 4,406,023 | 9/1983 | Harris | 3/1.912 |
| 4,435,854 | 4/1984 | Keller | 3/1.913 |
| 4,495,664 | 9/1985 | Blanquaert | 3/1.913 |
| 4,536,894 | 3/1985 | Galante | 623/22 |
| 4,589,883 | 5/1986 | Kenna | 623/23 |
| 4,608,055 | 8/1986 | Morrey et al. | 623/23 |
| 4,636,219 | 6/1987 | Pratt et al. | 623/22 |
| 4,657,551 | 4/1987 | Ecke | 623/23 |
| 4,657,552 | 6/1987 | Kanpf | 623/23 |
| 4,695,283 | 9/1987 | Aldinger | 623/23 |
| 4,718,912 | 1/1988 | Crowninshield | 623/22 |
| 4,738,681 | 6/1988 | Koeneman et al. | 623/23 |

FOREIGN PATENT DOCUMENTS 2153233  5/1985  United Kingdom .

OTHER PUBLICATIONS

Collarless H6P Femoral Prosthesis, Zimmer, 1986, The PCA Total Hip System, Howmedica, JBJS, Jun. 1984.
APR Universal Hip System, Intermedics, 1984, Integrated Systems of Inplants & Instrumentation Osteonics, 1984.
H52P Micro-Structured Hip System, Osteonics, 1984, Anatomic Hip Endoprosthesis System-Lubeck, S&6 Implants.
Opti-Fix Porous Coated Hip System, Richards, JBJS, Feb. 1987, 69A, Exclusive . . . The AML Total Hip System, Delay, JBJS, Jan. 1987.

Primary Examiner—Richard J. Apley
Assistant Examiner—David J. Isabella
Attorney, Agent, or Firm—Paul D. Schoenle

[57] ABSTRACT

A femoral component for a hip prosthesis includes a proximal end shaped in an anatomic manner to form asymmetrical sides. In particular, a lateral side forms an acute angle with an anterior side and a medial side forms an arcuate surface.

3 Claims, 2 Drawing Sheets

FEMORAL COMPONENT FOR A HIP PROSTHESIS

The present invention relates to a femoral component for a hip prosthesis to be used in hip arthroplasty. It is possible to reduce and/or eliminate severe pain in hip joints as a result of arthritis or other infirmities by implanting a stem within a femoral intramedullary canal. A ball on the proximal end of the stem cooperates with a socket of an acetabulum to provide for articulation between the femur and the acetabulum after the femoral head has been resected and the intramedullary canal has been cleared of cancellous bone proximally and fatty tissue distally. In order to maintain pain-free articulation of the hip joint following implantation of the stem, it is important that the stem be securely fastened to the intramedullary canal. Such fastening can be accomplished with a bone cement which adheres to the stem and the wall of the intramedullary canal. In addition, numerous stems have been provided with a porous surface as taught by U.S. Pat. No. 3,605,123 to either accommodate adherence with the bone cement or enhance a press fit between the porous surface and the wall of the intramedullary canal. If a press fit is desired with the intramedullary canal, the stem contour should closely match the contour of the intramedullary canal so that the porous surface is in intimate contact with bone, thereby enabling bone to grow into the porous surface.

In an attempt to design a femoral component for a press fit attachment to the wall of an intramedullary canal, U.S. Pat. No. 4,589,883 (Kenna) teaches a proximal portion which is elliptical in cross section with its major and minor axes twisting along a proximal direction. Consequently, a symetrical contour is provided for at each cross section of the femoral component in the Kenna patent. A different approach to matching the contour of the intramedullary canal is taught by U.S. Pat. No. 4,435,854 (Keller) wherein the longitudinal axis of the femoral component is imparted with a curvature in the anterior-posterior plane in the form of an S-shape. Although these patents address the issue of a femoral component to closely fit the intramedullary canal, it is believed that the anatomic structure for the intramedullary canal does not lend itself to a symmetrical femoral component.

It is an object of the present invention to provide a femoral component which more accurately reflects the anatomic contour for the intramedullary canal.

In the present invention, a femoral component for a hip prosthesis includes a proximal portion with an asymmetric contour to define an anterior side which forms an acute angle with a lateral side and the posterior side approaches the anterior side in the direction of the medial side. Furthermore, the medial side is arcuate in shape while the other sides include linear edges in cross section.

Figure 5:
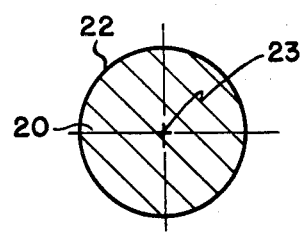
FIGS. 5-8 are cross sectional views taken along lines 5-8 of FIGS. 1 and 2.

A femoral component 10 includes a distal end 12 and a proximal end 14. As is well known, the femoral component is intended to fit within an intramedullary canal of a femur (not shown) such that the proximal end extends outwardly from the intramedullary canal of the femur to cooperate with an acetabulum via a ball or the like carried at the proximal end 14. A distal portion 16 includes a plurality of grooves 18 extending longitudinally. A center portion 20 defines a circular outer surface 22 as shown in FIG. 5 such that a straight longitudinal axis 23 intersects the center portion 20. A proximal portion 24 includes a porous surface 26 encircling the femoral component and a neck 28 adapted to carry a ball 30 shown in phantom in FIG. 1. An aperture 31 adjacent the neck 28 accommodates a tool for removing the femoral component from the intramedullary canal. The porous surface 26 is designed to extend outwardly from the proximal portion albeit a small extension of about 0.5 mm past the adjacent smooth surface of the proximal portion.

Figure 1:
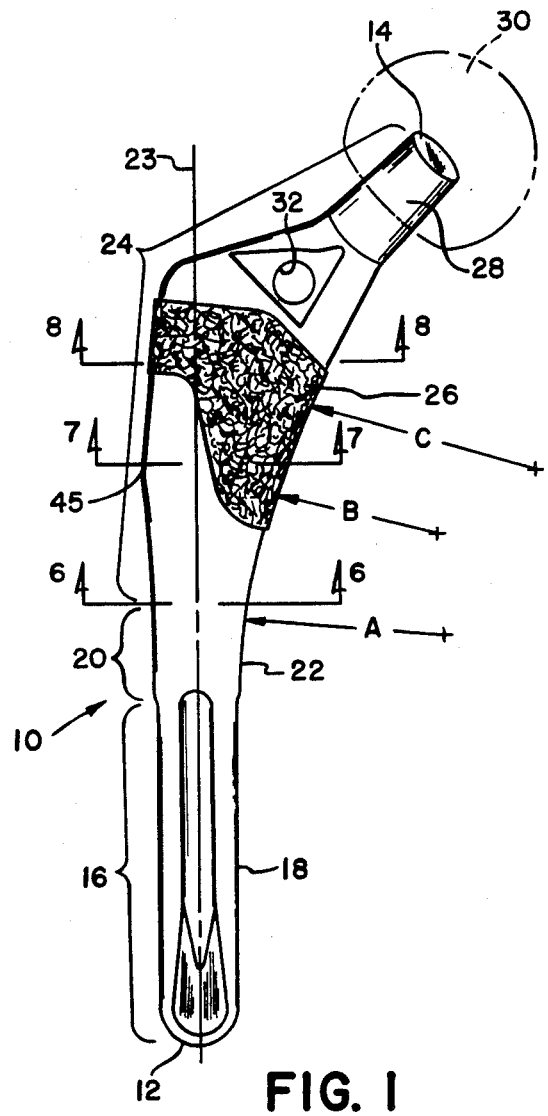
FIG. 1 is a side view of the femoral component of the present invention as contemplated for a right femur.
Figure 2:
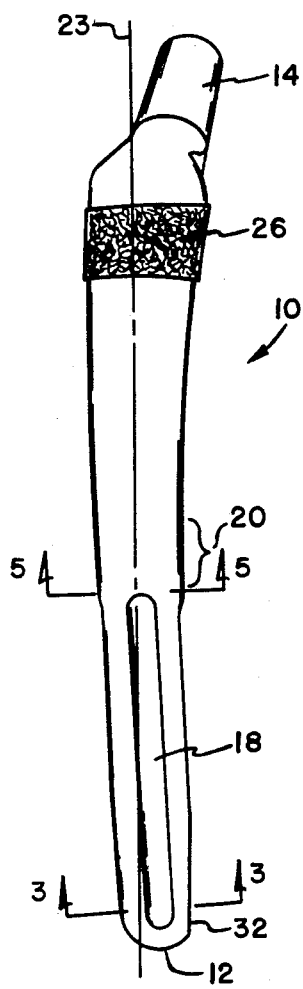
FIG. 2 is a left side view of FIG. 1.
Figure 3:
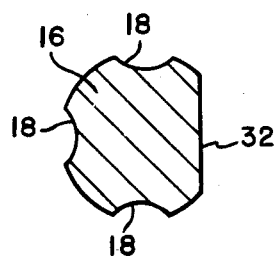
FIG. 3 is a cross sectional view taken along line 3—3 of FIG. 2.
Figure 4:
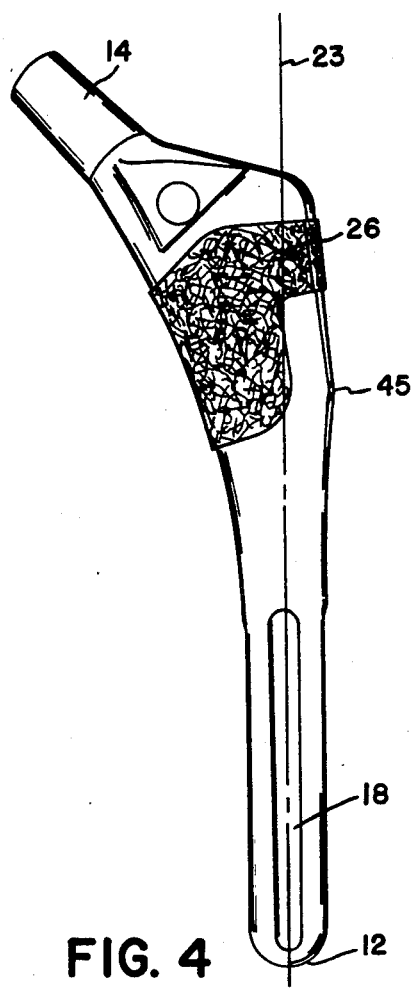
FIG. 4 is a back view of FIG. 1.

As shown in FIG. 2, the proximal portion 24 and the distal portion 16 bend in an anterior direction while the center portion 20 is in alignment with the longitudinal axis 23. FIG. 3 illustrates a chamfer 32 on the anterior side to avoid impingement of the distal end 12 into the bone surrounding the intramedullary canal at that location. FIGS. 1 and 4 illustrate a compound medial curve to accommodate a closer fit between the component 10 and an intramedullary canal. In this regard a first portion of the compound medial curve adjacent center portion 20 defines an arc with a radius A. A second portion of the compound medial curve defines an arc with a radius A, smaller than B, and a third portion of the compound medial curve defines an arc with a radius C smaller than B. The changes in radii appear slight for each of the three arc portions of the compound medial curve, however, these changes are believed to more accurately fill the intramedullary canal so that the desired press fit of the femoral component within the intramedullary canal provies for contiguous engagement of the femoral component with substantially all of the wall of the intramedullary canal adjacent the medial curve.

Figure 6:
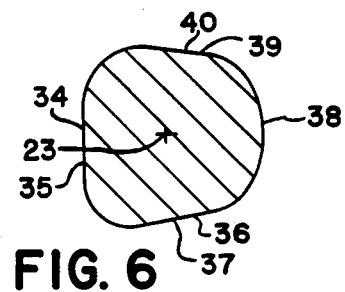
Figure 7:
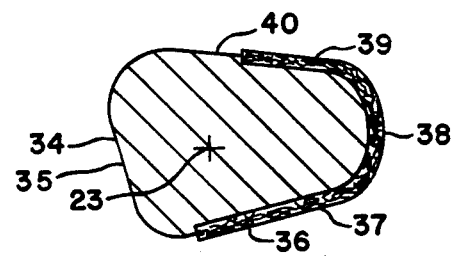
Figure 8:
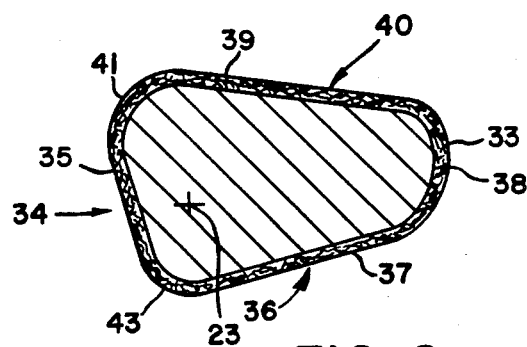

Turning to FIGS. 6-8, the proximal portion 24 defines an asymmetrical contour illustrated by a lateral side 34, a posterior side 36, a medial side 38 and an anterior side 40. Throughout the proximal portion 24, the medial side 38 defines an arcuate surface with a varying radius of curvature that generates an arcuate bulge 33 (see FIG. 8) near the anterior side at a proximal location coinciding with cross-sectional line 8—8 in FIG. 1. The lateral, posterior and anterior sides define linear edges 35, 37, and 39, respectively, in cross section with arcuate corners 41 and 43 therebetween. The anterior linear edge 39 cooperates with the lateral linear edge 35 to form an acute angle of about 67° while the posterior linear edge 37 cooperates with the lateral linear edge 35 to form a slightly obtuse angle of about 93°. Consequently, the anterior side 40 approaches the posterior side 36 from the lateral side 34 to the medial side 38. To accommodate the angular orientation of the lateral edge 35, the posterior edge 37 and the anterior edge 39, the arcuate corner 41 defines an arc of curvature which is greater in length than an arc of curvature for the corner 43.

Figure 9:
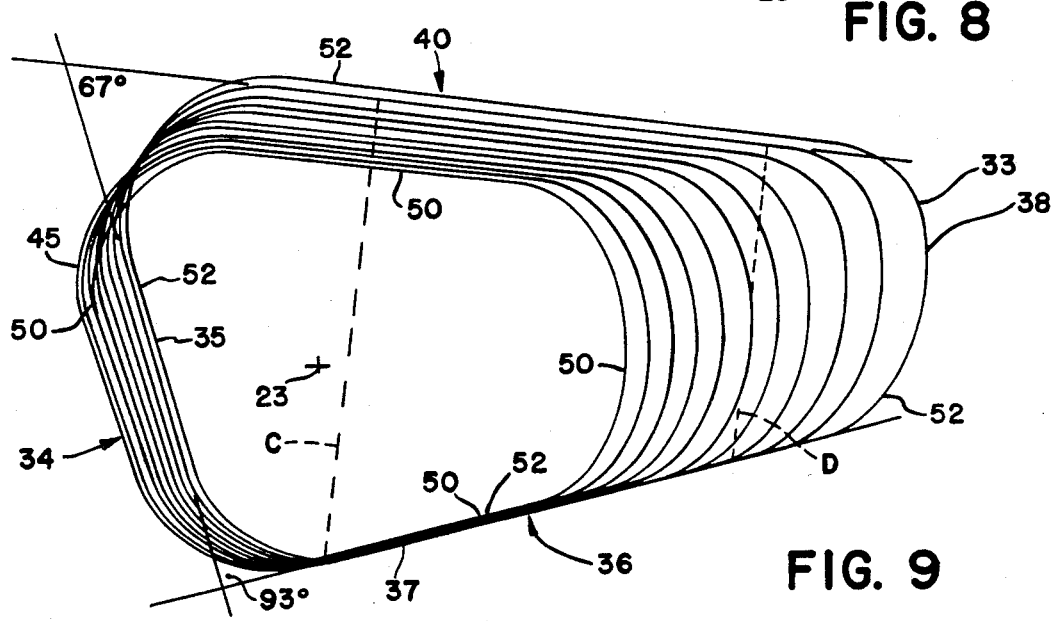
FIG. 9 is an overlay of numerous cross sectional views similar to FIGS. 5-8.

Turning to FIG. 9, a plurality of cross sectional views taken in the same manner as FIGS. 6-8 are overlayed with the longitudinal axis 23 indicated as a point of reference. The most distal cross section is shown at 50 and the most proximal cross section is shown at 52. The posterior side 36 shows the linear edges for cross sections 50 and 52 in alignment so that the posterior side 36 is substantially parallel with the longitudinal axis with only a slight curve, while the other sides are offset as described hereinafter. The posterior side has a curve albeit very slight so that the posterior side approaches the longitudinal axis 23 from the center portion 20 to the proximal portion 24, see FIG. 2. The radius of the posterior side curve is large, i.e. the change or movement of the surface toward the axis is small so that the posterior side edges appear to be coincident along the posterior face in FIG. 9. The lateral side 34 shows edges in cross section which initially extend away from the axis 23 to form a hump 45 (see FIGS. 1 and 4) as you move proximally away from cross section 50. As you continue moving proximally away from hump 45, the edges for the lateral side move toward the axis 23 in a linear manner. Between the hump 45 and the cross section 50, the lateral side 34 exhibits a transition from an arcuate edge as shown at FIG. 5, to a flat edge as shown at FIG. 6, to a flat angled edge as shown at FIG. 7. Between the hump 45 and the cross section 52, the lateral side 34 forms edges 35 in cross section which are parallel and approach axis 23. The anterior side 40 extends away from the longitudinal axis 23 from the distal cross section 50 to the proximal cross section 52. The distal cross section 50 for the medial side 38 illustrates a substantially circular arcuate edge while at the proximal cross section 52 for the medial side 38, the arcuate edge is distorted outwardly to for the bulge 33 near the anterior side 40.

In view of the foregoing description of femoral component 10, it is seen that the outer contour of the proximal portion 24 is designed asymmetrically to substantially match an anatomic envelope of the intramedullary canal. As a result, each side of the femoral component 10 in the proximal portion 24 includes its own distinct geometry. A femoral component constructed in this manner is believed to closely fit the intramedullary canal along its anatomic axis, thereby generating a substantially contiguous engagement between the femoral component and the wall of the intramedullary canal.

What we claim is:

1. A femoral component for a hip prosthesis having a distal end adapted for disposition within an intramedullary canal of the femur and a proximal end extending outwardly of the intramedullary canal for disposition adjacent an acetabulum, the femoral component defining a straight longitudinal axis and a proximal portion which substantially matches the contour of the intramedullary canal for a tight fit therein, the proximal portion including a porous surface to enhance fixation of the femoral component within the intramedullary canal, and the proximal portion further including substantially planar anterior, posterior, and lateral sides and a medial side a lateral side and a medial side, a cross section of the proximal portion forming substantially linear edges for the anterior, lateral and posterior sides while the cross section forms a substantially arcuate surface for the medial side to generate a predetermined asymmetric contour substantially matching a contour of the intramedullary canal of the femur, and the linear edge of the lateral side cooperates with the linear edge of the posterior side to form a slightly obtuse angle therebetween.

2. The femoral component of claim 1 in which the medial arcuate surface is substantially circular in shape distally and the medial arcuate surface is distorted at the proximal end to define a radius of curvature which varies from the posterior side to the anterior side.

3. A femoral component for a hip prosthesis having a distal end adapted to fit within a femoral intramedullary canal and a proximal end extending outwardly of the intramedullary canal to cooperate with an acetabulum, the femoral component including a proximal portion adjacent the proximal end to form a tight fit with a wall of the intramedullary canal, the proximal portion including a medial side which forms a substantially arcuate surface over the length of the proximal portion, the medial side including a distortion of the arcuate surface near the proximal end to form a bulge extending outwardly, and the proximal portion further includes substantially planar lateral and posterior sides cooperating with each other to form an obtuse angle therebetween, so that the proximal portion substantially matches an asymmetric contour of the intramedullary canal when in tight fit therewith.

* * * * *